United States Patent [19]

Rice

[11] Patent Number: 5,716,601
[45] Date of Patent: Feb. 10, 1998

[54] DENTIFRICE COMPOSITIONS

[75] Inventor: David Earl Rice, Cincinnati, Ohio

[73] Assignee: The Procter & Gamble Company, Cincinnati, Ohio

[21] Appl. No.: 620,766

[22] Filed: Mar. 22, 1996

[51] Int. Cl.⁶ .................... A61K 7/16; A61K 7/18
[52] U.S. Cl. ............................ 424/52; 424/49
[58] Field of Search ........................... 424/49–58

[56] References Cited

U.S. PATENT DOCUMENTS

| | | | |
|---|---|---|---|
| 3,003,919 | 10/1961 | Broge | 424/49 |
| 3,151,027 | 9/1964 | Cooley et al. | 167/93 |
| 3,325,368 | 6/1967 | Wood | 167/93 |
| 3,450,813 | 6/1969 | Muhler | 424/52 |
| 3,574,823 | 4/1971 | Roberts et al. | 424/49 |
| 3,955,942 | 5/1976 | Cordon et al. | 51/295 |
| 3,988,162 | 10/1976 | Wason | 106/288 |
| 3,989,814 | 11/1976 | Cordon et al. | 424/57 |
| 4,040,858 | 8/1977 | Wason | 106/288 B |
| 4,060,599 | 11/1977 | Cordon | 424/49 |
| 4,067,746 | 1/1978 | Wason et al. | 106/288 B |
| 4,075,316 | 2/1978 | Cordon | 424/49 |
| 4,089,943 | 5/1978 | Roberts et al. | 424/49 |
| 4,122,160 | 10/1978 | Wason | 424/49 |
| 4,141,969 | 2/1979 | Mitchell | 424/52 |
| 4,170,634 | 10/1979 | Cordon et al. | 424/49 |
| 4,174,387 | 11/1979 | Cordon et al. | 424/52 |
| 4,187,288 | 2/1980 | Cordon et al. | 424/49 |
| 4,340,583 | 7/1982 | Wason | 424/52 |
| 4,376,762 | 3/1983 | Hauschild et al. | 424/49 |
| 4,376,763 | 3/1983 | Barth et al. | 424/49 |
| 4,412,983 | 11/1983 | Mitchell | 424/52 |
| 4,632,826 | 12/1986 | Plöger et al. | 424/52 |
| 4,664,907 | 5/1987 | Müller | 424/52 |
| 4,704,270 | 11/1987 | Müller et al. | 424/49 |
| 4,705,679 | 11/1987 | Müller et al. | 424/52 |
| 4,988,369 | 1/1991 | Akay | 51/293 |
| 5,110,574 | 5/1992 | Reinhardt et al. | 423/335 |
| 5,279,815 | 1/1994 | Wason et al. | 424/52 |

OTHER PUBLICATIONS

U.S. application No. 08/312,353, Rice, filed Sep. 26, 1994.
U.S. application No. 08/434,149, Rice, filed May 2, 1995.
U.S. application No. 08/434,154, Rice, filed May 2, 1995.
U.S. application No. 08/434,147, Rice, filed May 2, 1995.

*Primary Examiner*—Shep K. Rose
*Attorney, Agent, or Firm*—Douglas C. Mohl; Jacobus C. Rasser; T. David Reed

[57] ABSTRACT

Oral compositions, such as oral gels and toothpastes, containing a novel abrasive.

14 Claims, No Drawings

DENTIFRICE COMPOSITIONS

TECHNICAL FIELD

The present invention relates to dentifrice compositions such as toothpastes, which provide improved oral cleaning.

BACKGROUND OF THE INVENTION

A satisfactory dentifrice composition should have a cosmetic effect upon the teeth, namely, keeping them light colored. It should also clean and remove debris as well, thereby aiding the prevention of tooth decay and promoting gingival health. Abrasives aid in the removal of the tightly adherent pellicle film. This film usually comprises a thin acellular, glycoprotein-mucoprotein coating which adheres to the enamel within minutes after teeth are cleaned. The presence of various food pigments lodged within the film accounts for most instances of teeth discoloration. Ideally, an abrasive should provide satisfactory removal (cleaning) of the pellicle film with minimal damage (abrasion) to oral tissue, i.e. the dentin and enamel.

Beyond the pellicle cleaning aspect, incorporating an antiplaque agent(s) provides additional benefits. The formation of dental plaque is the primary source of dental caries, gingival and periodontal disease, and tooth loss. Plaque is a mixed matrix of bacteria, epithelial cells, leukocytes, macrophages and other oral exudate The bacteria associated with plaque can secrete enzymes and endotoxins which can irritate the gums and cause an inflammatory gingivitis. As the gums become increasingly irritated by this process, they have a tendency to bleed, lose their toughness and resiliency, and separate from the teeth. This separation results in periodontal pockets leading in turn to further accumulation of debris, secretions, and more bacteria/toxins. This process eventually leads to destruction of both the hard and soft tissue of the oral cavity.

The use of a variety of agents to clean the oral cavity and reduce plaque and mouth malodor has been recognized for some time. Examples include: U.S. Pat. No. 3,696,191, Oct. 3, 1972 to Weeks; U.S. Pat. No. 3,991,177, Nov. 9, 1976 to Vidra et al.; U.S. Pat. No. 4,058,595, Nov. 15, 1977 to Colodney; U.S. Pat. No. 4,115,546, to Vidra et al.; U.S. Pat. No. 4,138,476, Feb. 6, 1979 to Simonson et al.; U.S. Pat. No. 4,140,758, Feb. 20, 1979 to Vidra et al.; U.S. Pat. No. 4,154,815, May 15, 1979 to Pader; U.S. Pat. No. 4,737,359, Apr. 12, 1988 to Eigen et al.; U.S. Pat. No. 4,986,981, Jan. 22, 1991 to Glace et al.; U.S. Pat. No. 4,992,420, Feb. 12, 1991 to Nesser; U.S. Pat. No. 5,000,939, Mar. 19, 1991 to Dring et al.; Kokai 02/105,898, published Apr. 18, 1990 to Kao Corporation; Kokai 03/128,313, published May 31, 1991 to Nippon Kotai Kenkyu and Kokai 03/223,209, published Oct. 2, 1991 to Lion Corporation; U.S. Pat. No. 4,652,444, Mar. 24, 1987 to Maurer; U.S. Pat. No. 4,725,428, Feb. 16, 1988 to Miyahara et al.; U.S. Pat. No. 4,355,022, Oct. 19, 1982 to Rabussay and PCT application WO 86/02831, published May 22, 1986 to Zetachron, Inc.

Abrasives are described in U.S. Pat. No. 4,340,583, Jul. 20, 1982 to Wason, U.S. Pat. No. 3,574,823, Apr. 13, 1971 to Roberts et al., EP Patent 535,943A1, Apr. 7, 1993, McKeown et al., and PCT Patent WO 92/02454, Feb. 20, 1992 to McKeown et al.

In spite of the many disclosures relating to compositions for pellicle cleaning and antiplaque activity, the need for improved products still exists. The present inventor has developed oral compositions providing improved pellicle cleaning. Specifically, the present inventor has developed oral compositions incorporating a novel silica abrasive and an improved plaque reducing system.

It is therefore an object of the present invention to provide an oral care product and methods of using the same directed at pellicle cleaning. It is a further object of the present invention to provide compositions and methods which are effective in arresting the accumulation of plaque and preventing gum disease. A still further object of the present invention is to provide compositions that will also abate subsequent calculus formation.

These objectives and additional objectives will become readily apparent from the detailed description which follows.

SUMMARY OF THE INVENTION

The present invention relates to dentifrice compositions comprising:

a. a precipitated silica wherein the silica has a 40% slurry viscosity build of less than 20,000 centipoise and a 10% Brass Einlehner abrasion of approximately 2.5 to 20.0 mg loss/100,000 revolutions; and b. from about 0.1% to about 99% of an orally-acceptable dentifrice carrier.

The present invention further relates to a method of cleaning teeth reducing plaque, gingivitis and calculus using the above compositions.

All percentages and ratios herein are by weight unless otherwise specified. PCR and RDA are unitless. Additionally, all measurements are made at 25° C. unless otherwise specified.

DETAILED DESCRIPTION OF THE INVENTION

By "safe and effective amount," as used herein, means a sufficient amount to reduce stain and/or plaque/gingivitis without harming the tissues and structures of the oral cavity.

By the term "orally-acceptable carrier," as used herein, means a suitable vehicle which can be used to apply the present compositions to the oral cavity in a safe and effective manner.

The pH of the present herein described compositions range from about 6.5 to about 9.5, with the preferred pH being from about 6.5 to about 9.0 and the most preferred pH being 7.0 to about 9.0.

The essential as well as optional components of the compositions of the present invention are described in the following paragraphs.

Abrasive

The present invention utilizes novel amorphous precipitated silica compositions which are useful to impart improved cleaning and abrasive characteristics to dentifrice formulations. The silicas of the present invention are preferably characterized as synthetic hydrated amorphous silicas also know as silicon dioxides of $SiO_2$. In particular, the silicas of the present invention have smaller reactor slurry average particle sizes (APS) than known silicas. Silicas of the present invention also have a significantly lower viscosity build than known silicas of comparable abrasiveness. Accordingly, silicas of the present invention may be loaded into dentifrice compositions in greater concentrations than known silicas, resulting in dentifrice compositions with improved properties and without undue abrasiveness.

Reactor slurry APS is defined as the APS of the precipitated silica compositions as measured after processing in the reactor or washed slurry but before drying, milling, and/or use. Reactor slurry APS is measured using a Microtrac II Particle Analyzer manufactured by Leeds and Northrup. Silicas of the present invention preferably have a reactor slurry APS of approximately 10 to 50 μm, and more preferably approximately 10 to 20 μm. All reactor slurry APS values provided herein are median values ("50%") unless otherwise indicated.

Without limiting itself to any particular theory, it is believed that the relatively low reactor slurry APS results in the preparation of silicas with relatively low average functional particle size, where functional particle size is defined as the particle size of the silica while it is in use (e.g., during the brushing process). In other words, Applicant believes that the silicas of the present invention are softer than silicas with higher reactor slurry APS. As a result, Applicant believes that, in use, the silicas of the present invention (i.e., with relatively low reactor slurry APS) break up into smaller and, therefore, less abrasive particles more readily than silicas with higher reactor slurry APS. The silicas of the present invention are, therefore less abrasive than known silicas with the same milled APS. In addition, silicas of the present invention have improved milling properties because they are initially smaller and require less milling, and because they are softer and, therefore, tend to break up into smaller particles more readily. As a result, silicas of the present invention are less likely to suffer from the graying caused by excessive milling.

Silicas used in the present invention are also relatively less abrasive than known silicas of approximately the same milled APS and viscosity build. Several tests are used to measure abrasiveness of silicas. The most direct measure is the Brass Einlehner Abrasion test. In the Brass Einlehner Abrasion test, an Einlehner AT-1000 Abrader is used as follows: (1) a Fourdrinier brass wire screen is weighed and exposed to the action of a 10% aqueous silica suspension for a fixed length of time; (2) the amount of abrasion is then determined as milligrams brass lost from the Fourdrinier wire screen per 100,000 revolutions. 10% Brass Einlehner (10% BE) results are expressed in milligrams loss/100,000 revolutions. Silicas in accordance with the present invention have 10% BE values of approximately 3.5 to 5.0 mg loss/100,000 revolutions, and more preferably approximately 3.5 to 4.5 mg loss/100,000 revolutions.

Silicas used in the present invention also tend to have a relatively small impact on viscosity of dentifrice compositions compared to known silicas. The tendency of a silica to increase the viscosity of a fluid is referred to as "viscosity build." Viscosity may be measured by a viscosimeter and may be expressed in centipoises. In a 40% slurry test, silicas in accordance with the present invention, having a moisture content of 5 to 7% and where moisture is measured by weight loss at 105° C. for 2 hours, have a viscosity of about 5,000 to about 12,000 centipoises.

Silicas used in the present invention are preferably Low Structure silicas in accordance with the definitions set forth in the J. Soc. Cosmet. Chem. 29, 497–521 (Aug., 1978) and Pigment Handbook: Volume 1, Properties and Economics, Second Edition, Edited by Peter A. Lewis, John Wiley & Sons, Inc., 1988, p. 139–159.

Silicas used in the present invention preferably have an oil absorption in the range of approximately 60 to 120 cc/100g and more preferably approximately 80 to 100 cc/100 g, and most preferably approximately 80 to 90 cc/100 g. In the present specification oil absorption is measured using the ASTM rub-out method D281.

Silicas used in the present invention preferably have a BET surface area in the range of approximately 50 to 250 $m^2/g$. Surface area is determined by the BET nitrogen adsorption method of Brunaur et al., *J. Am. Chem. Soc.*, 60, 309 (1938).

Silicas used in the present invention also preferably exhibit fluoride availability and compatibility values in the range of approximately 90–100%, as defined in U.S. Pat. No. 4,340,583, which is incorporated by reference herein.

Silicas used in the present invention preferably have mercury intrusion void volume values in the range of 1.0 to 4.0 cc/g and more preferably 1.2 to 2.0 cc/g. The pore volumes (mercury pore volume) are determined using an Autopore II 9220 Porosimeter (Micromeritics Corporation). This instrument measure the void volume and pore size distribution of various materials. Mercury is forced into the voids as a function of pressure and the volume of mercury intruded per gram of sample is calculated at each pressure setting. Total pore volume expressed herein represents the cumulative volume of mercury intruded at pressures from vacuum to 60,000 psi. Increments in volume (cc/g) at each pressure setting are plotted against the pore radius corresponding to the pressure setting increments. The peak in the intruded volume versus pore radius curve corresponds to the mode in the pore size distribution and identifies the most common pore size in the sample.

Silicas used in the present invention preferably have a pH of approximately 4.0 to 8.5 and more preferably from 6.5 to 8.5, as measured in a 5% aqueous slurry.

Silicas used in the present invention preferably have a Pellicle Cleaning Ration (PCR) of approximately 70 to 140 and preferably approximately 100 to 130.

Silicas used in the present invention preferably have a pour density of approximately 15–25 $lb./ft^3$ and a pack density of approximately 25–35 $lb./ft^3$. Bulk density is measured by measuring the volume in liters occupied by a given weight of the silica, and is reported in pounds per cubic foot.

Silicas used in the present invention preferably have a brightness value of approximately 90 to 100. To measure brightness, fine powder materials are pressed into a smooth surfaced pellet and are evaluated using a Technidyne Brightimeter S-5/BC. The Technidyne Brightimeter S-5/BC has a dual beam optical system where the sample is illuminated at an angle of 45°, and the reflected light viewed at 0°. This method conforms to TAPPI test methods T452 and T646, and ASTM Standard D985.

Preferred precipitated silica materials include those available from the J.M. Huber Corporation under the tradename, "Zeodent", particularly the silica carrying the designation "Zeodent 128" and "Zeodent 118".

The abrasive in the compositions described herein is present at a level of from about 6% to about 70%, preferably from about 15% to about 35% when the dentifrice is a toothpaste. Higher levels, as high as 95%, may be used if the composition is a toothpowder.

In addition to the above described essential components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, Apr. 2, 1991 to Majeti; U.S. Pat. No. 4,885,155, Dec. 5, 1989 to Parran, Jr. et al.; U.S. Pat. No. 3,959,458, May 25, 1976 to Agricola et al. and U.S. Pat. No. 3,937,807, Feb. 10, 1976 to Haefele, all being incorporated herein by reference.

PHARMACEUTICALLY ACCEPTABLE CARRIER

The carrier for the components of the present compositions can be any dentifrice vehicle suitable for use in the oral cavity. Such carriers include the usual components of toothpastes, tooth powders, prophylaxis pastes, lozenges, gums and the like and are more fully described hereinafter. Toothpastes are the preferred systems.

Surfactants

One of the preferred optional agents of the present invention is a surfactant, preferably one selected from the group consisting of sarcosinate surfactants, isethionate surfactants and taurate surfactants. Preferred for use herein are alkali metal or ammonium salts of these surfactants. Most preferred herein are the sodium and potassium salts of the following: lauroyl sarcosinate, myristoyl sarcosinate, palmitoyl sarcosinate, stearoyl sarcosinate and oleoyl sarcosinate.

This surfactant can be present in the compositions of the present invention from about 0.1% to about 2.5%, preferably from about 0.3% to about 2.5% and most preferably from about 0.5% to about 2.0% by weight of the total composition.

Other suitable compatible surfactants can optionally be used along with the sarcosinate surfactant in the compositions of the present invention. Suitable optional surfactants are described more fully in U.S. Pat. No. 3,959,458, May 25, 1976 to Agricola et al.; U.S. Pat. No. 3,937,807, Feb. 10, 1976 to Haefele; and U.S. Pat. No. 4,051,234, Sep. 27, 1988 to Gieske et al. These patents are incorporated herein by reference.

Preferred anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixtures of anionic surfactants can also be utilized.

Preferred cationic surfactants useful in the present invention can be broadly defined as derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. Preferred compounds are the quaternary ammonium fluorides described in U.S. Pat. No. 3,535,421, Oct. 20, 1970, to Briner et al., herein incorporated by reference, where said quaternary ammonium fluorides have detergent properties. Certain cationic surfactants can also act as germicides in the compositions disclosed herein. Cationic surfactants such as chlorhexadine, although suitable for use in the current invention, are not preferred due to their capacity to stain the oral cavitys hard tissues. Persons skilled in the art are aware of this possibility and should incorporate cationic surfactants only with this limitation in mind.

Preferred nonionic surfactants that can be used in the compositions of the present invention can be broadly defined as compounds produced by the condensation of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Preferred zwitterionic synthetic surfactants useful in the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

Preferred betaine surfactants are disclosed in U.S. Pat. No. 5,180,577 to Polefka et al., issued Jan. 19, 1993. Typical alkyl dimethyl betaines include decyl betaine or 2-(N-decyl-N,N-dimethylammonio) acetate, coco betaine or 2-(N-coc-N, N-dimethyl ammonio) acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice are preferably the cocoamidopropyl betaine and, more preferably, the lauramido propyl betaine.

Chelating Agents

Another preferred optional agent is a chelating agent selected from the group consisting of tartaric acid and pharmaceutically-acceptable salts thereof, citric acid and alkali metal citrates and mixtures thereof. Chelating agents are able to complex calcium found in the cell walls of the bacteria. Chelating agents can also disrupt plaque by removing calcium from the calcium bridges which help hold this biomass intact. However, it is possible to use a chelating agent which has an affinity for calcium that is too high. This results in tooth demineralization and is contrary to the objects and intentions of the present invention.

Sodium and potassium citrate are the preferred alkali metal citrates, with sodium citrate being the most preferred. Also preferred is a citric acid/alkali metal citrate combination. Preferred herein are alkali metal salts of tartaric acid. Most preferred for use herein are disodium tartrate, dipotassium tartrate, sodium potassium tartrate, sodium hydrogen tartrate and potassium hydrogen tartrate. The amounts of chelating agent suitable for use in the present invention are about 0.1% to about 2.5%, preferably from about 0.5% to about 2.5% and more preferably from about 1.0% to about 2.5%. The tartaric acid salt chelating agent can be used alone or in combination with other optional chelating agents.

Other optional chelating agents can be used. Preferably these chelating agents have a calcium binding constant of about $10^1$ to $10^5$ provide improved cleaning with reduced plaque and calculus formation.

Another group of agents suitable for use as chelating agents in the present invention are the soluble pyrophosphates. The pyrophosphate salts used in the present compositions can be any of the alkali metal pyrophosphate salts. Specific salts include tetra alkali metal pyrophosphate, dialkali metal diacid pyrophosphate, trialkali metal monoacid pyrophosphate and mixtures thereof, wherein the alkali metals are preferably sodium or potassium. The salts are useful in both their hydrated and unhydrated forms. An effective amount of pyrophosphate salt useful in the present composition is generally enough to provide at least 1.0% pyrophosphate ion, preferably from about 1.5% to about 6%, more preferably from about 3.5% to about 6% of such ions. It is to be appreciated that the level of pyrophosphate ions is that capable of being provided to the composition (i.e., the theoretical amount at an appropriate pH) and that pyrophosphate forms other than $P_2O_7\text{-}4$ (e.g., ($HP_2O_7\text{-}3$)) may be present when a final product pH is established.

The pyrophosphate salts are described in more detail in Kirk & Othmer, *Encyclopedia of Chemical Technology*, Second Edition, Volume 15, Interscience Publishers (1968), incorporated herein by reference.

Still another possible group of chelating agents suitable for use in the present invention are the anionic polymeric polycarboxylates. Such materials are well known in the art, being employed in the form of their free acids or partially or preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and preferably S-97 Pharmaceutical Grade (M.W. 70,000), of GAF Chemicals Corporation.

Other operative polymeric polycarboxylates include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates are disclosed in U.S. Pat. No. 4,138,477, Feb. 6, 1979 to Gaffar and U.S. Pat. No. 4,183,914, Jan. 15, 1980 to Gaffar et al. both patents are incorporated herein by reference, and include copolymers of maleic anhydride with styrene, isobutylene or ethyl vinyl ether, polyacrylic, polyitaconic and polymaleic acids, and sulfoacrylic oligomers of M.W. as low as 1,000 available as Uniroyal ND-2.

Flavoring agents can also be added to dentifrice compositions. Suitable flavoring agents include oil of wintergreen, oil of peppermint, oil of spearmint, oil of sassafras, and oil of clove. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Dentifrice compositions can also contain emulsifying agents. Suitable emulsifying agents are those which are reasonably stable and foam throughout a wide pH range, including non-soap anionic, nonionic, cationic, zwitterionic and amphoteric organic synthetic detergents. Many of these suitable surfactants are disclosed by Gieske et al, in U.S. Pat. No. 4,051,234, Sep. 27, 1977, incorporated herein by reference.

It is common to have an additional water-soluble fluoride compound present in dentifrices and other oral compositions in an amount sufficient to give a fluoride ion concentration in the composition at 25° C., and/or when it is used of from about 0.0025% to about 5.0% by weight, preferably from about 0.005% to about 2.0% by weight, to provide additional anticaries effectiveness. A wide variety of fluoride ion-yielding materials can be employed as sources of soluble fluoride in the present compositions. Examples of suitable fluoride ion-yielding materials are found in U.S. Pat. No. 3,535,421, Oct. 20, 1970 to Briner et al. and U.S. Pat. No. 3,678,154, Jul. 18, 1972 to Widder et al., both being incorporated herein by reference. Representative fluoride ion sources include: stannous fluoride, sodium fluoride, potassium fluoride, sodium monofluorophosphate and many others. Stannous fluoride and sodium fluoride are particularly preferred, as well as mixtures thereof.

Water is also present in the toothpastes of this invention. Water employed in the preparation of commercially suitable toothpastes should preferably be deionized and free of organic impurities. Water generally comprises from about 10% to 50%, preferably from about 20% to 40%, by weight of the toothpaste compositions herein. These amounts of water include the free water which is added plus that which is introduced with other materials such as with sorbitol.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, xanthan gun, gum arabic, and gum tragacanth can also be used. Thickening agents in an amount from 0.5% to 5.0% by weight of the total composition can be used.

It is also desirable to include some humectant material in a toothpaste to keep it from hardening. Suitable humectants include glycerin, sorbitol, and other edible polyhydric alcohols at a level of from about 15% to about 70%.

Also desirable for inclusion in the compositions of the present invention are other stannous salts such as stannous pyrophosphate and stannous gluconate and antimicrobials such as quaternary ammonium salts, such as cetyl pyridinium chloride and tetradecylethyl pyridinium chloride, bisbiquanide salts, copper bisglycinate, nonionic anti microbial salts and flavor oils. Such agents are disclosed in U.S. Pat. No. 2,946,725, Jul. 26, 1960, to Norris et al. and U.S. Pat. No. 4,051,234, Sep. 27, 1977 to Gieske et al., incorporated herein by reference. Other optional components include buffering agents, bicarbonates, peroxides, nitrate salts such as sodium and potassium nitrate. These agents, if present, are included at levels of from about 0.01% to about 30%.

Other useful carriers include biphasic dentifrice formulations such as those disclosed in U.S. Pat. Nos. 5,213,790, issued May 23, 1993, 5,145,666, issued Sep. 8, 1992, and 5,281,410 issued Jan. 25, 1994 all to Lukacovic et al. and in U.S. Pat. Nos. 4,849,213 and 4,528,180 to Schaeffer the disclosures of which are incorporated by reference herein.

Suitable lozenge and chewing gum components are disclosed in U.S. Pat. No. 4,083,955, Apr. 11, 1978 to Grabenstetter et al., incorporated herein by reference.

The following examples further describe and demonstrate preferred embodiments within the scope of the present invention. The examples are given solely for illustration and are not to be construed as limitations of this invention as many variations are possible without departing from the spirit and scope thereof.

EXAMPLE I

A dentifrice composition of the present invention contains the following components as described below.

| Component | Wgt % |
|---|---|
| Sorbitol 70% soln | 24.200 |
| RO Water | 24.757 |
| Glycerin | 7.000 |
| Carboxymethyl Cellulose[1] | 0.500 |
| PEG 6 | 4.000 |
| Sodium Fluoride | 0.243 |
| Sodium Saccharine | 0.130 |
| Monosodium Phosphate | 0.415 |
| Trisodium Phosphate | 0.395 |
| Sodium Tartrate | 1.000 |
| TiO2 | 0.500 |
| Silica[2] | 35.000 |
| Sodium Lauroyl Sarcosinate (95% active) | 1.060 |
| Flavor | 0.800 |

[1]Supplied by Aqualon Company.
[2]Available as Zeodent 118 from J. M. Huber Corporation The jacket temperature of a mixing tank is set to about 150° F. (65° C.) to about 160° F. (71° C.). The humectants and water are added to the mixing tank and agitation is started. When the temperature reaches approximately 120° F. (50° C.) fluoride, sweetening agents, buffering agents, chelant, coloring agents and titanium dioxide are added. Thickening agents are added to the abrasive and the resulting mixture is added to the mixing tank with high agitation. The surfactant is added to the combination and mixing is continued. The tank is cooled to 120° F. (50° C.) and the flavoring agents are added. Mixing is continued for approximately 5 minutes. The resulting composition will have a pH of about 7.

EXAMPLE II

A dentifrice composition of the present invention contains the following components as described below.

| Component | Wgt % |
|---|---|
| Sorbitol 70% soln | 29.810 |
| RO Water | 24.757 |
| Glycerin | 7.000 |
| Carboxymethyl Cellulose[1] | 0.750 |
| PEG 6 | 4.000 |
| Sodium Fluoride | 0.243 |
| Sodium Saccharine | 0.130 |
| Monosodium Phosphate | 0.415 |
| Trisodium Phosphate | 0.395 |
| TiO2 | 0.500 |
| Silica[2] | 30.000 |
| Sodium Lauryl Sulfate | 1.200 |
| Flavor | 0.800 |

[1]Supplied by Aqualon Company.
[2]Available as Zeodent 128 from J. M. Huber Corporation.

EXAMPLE III

A gum composition of the present invention contains the following components as described below.

| Component | Weight % |
|---|---|
| Gum Base<br>30 parts Estergum<br>45 parts Coumorone Resin<br>15 parts Dry Latex | 30.000 |
| Silica[1] | 10.00 |
| Sugar | 40.000 |
| Corn Syrup | 18.175 |
| Sodium Lauroyl Sarcosinate | 0.075 |
| Sodium Tartrate | 0.250 |
| Flavor | 1.500 |

[1]Zeodent 118.

What is claimed is:

1. A dentifrice composition comprising:

a. a precipitated silica wherein the silica has a 40% slurry viscosity build of about 5,000 to about 12,000 centipoise and a 10% Brass Einlehner abrasion of approximately 3.5 to about 5.0 mg loss/100,000 revolutions; and b. from about 0.1% to about 99% of an orally-acceptable dentifrice carrier.

2. A dentifrice composition according to claim 1 wherein said abrasive a 10% Brass Einlehner Abrasion Value of about 3.5 to about 4.5 mg loss/100,000 revolutions.

3. A dentifrice composition according to claim 2, wherein the median average particle size of said particles ranges from about 7 to 11 microns.

4. A dentifrice composition according to claim 3 wherein said composition further comprising a fluoride ion source wherein the fluoride ion source is selected from the group consisting of sodium fluoride, stannous fluoride, sodium monofluorophosphate, potassium fluoride and mixtures thereof.

5. A dentifrice composition according to claim 4 which further comprises a surfactant selected from the group consisting of sarcosinate surfactants, isethionate surfactants and taurate surfactants.

6. A dentifrice composition according to claim 5 which further comprises from about 0.1% to about 2.5% of a chelating agent selected from the group consisting of tartaric acid and pharmaceutically-acceptable salts thereof, citric acid and alkali metal citrates and mixtures thereof.

7. A dentifrice composition according to claim 6 wherein said composition has a pH above about 7 and wherein the surfactant is selected from the group consisting of sodium lauroyl sarcosinate, sodium decyl sarcosinate, sodium myristyl sarcosinate, sodium stearyl sarcosinate, sodium palmitoyl sarcosinate, sodium oleoyl sarcosinate and mixtures thereof.

8. A dentifrice composition according to claim 7 further comprising from about 15% to about 70% of a humectant selected from among the group consisting of glycerin, sorbitol, Propylene glycol and mixtures thereof.

9. A dentifrice composition according to claim 8 wherein the surfactant is a combination of sodium lauroyl sarcosinate and cocoamidopropyl betaine and the chelating agent is a combination of tartaric acid and sodium tartrate.

10. A dentifrice composition according to claim 1 in the form of a toothpaste, tooth powder, prophylaxis paste, lozenge, gum, or oral gel.

11. A method for reducing stain and/or plaque and gingivitis comprising the application of a safe and effective amount of a composition according to claim 1, to the teeth and other oral surfaces.

12. A method for reducing stain and/or plaque and gingivitis comprising the application of a safe and effective amount of a composition according to claim 4, to the teeth and other oral surfaces.

13. A method for reducing stain and/or plaque and gingivitis comprising the application of a safe and effective amount of a composition according to claim 7, to the teeth and other oral surfaces.

14. A method for reducing stain and/or plaque and gingivitis comprising the application of a safe and effective amount of a composition according to claim 10, to the teeth and other oral surfaces.

* * * * *